(12) United States Patent
Brennan et al.

(10) Patent No.: US 9,823,261 B2
(45) Date of Patent: Nov. 21, 2017

(54) MULTI-WELL WEDGE-SHAPED REAGENT CONTAINER WITH AUTO-OPEN CAPABILITY

(71) Applicant: Siemens Healthcare Diagnostics Inc., Tarrytown, NY (US)

(72) Inventors: Joseph Brennan, Newark, DE (US); James Kegelman, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 15/034,608

(22) PCT Filed: Oct. 30, 2014

(86) PCT No.: PCT/US2014/063232
§ 371 (c)(1),
(2) Date: May 5, 2016

(87) PCT Pub. No.: WO2015/069546
PCT Pub. Date: May 14, 2015

(65) Prior Publication Data
US 2016/0266155 A1 Sep. 15, 2016

Related U.S. Application Data

(60) Provisional application No. 61/900,209, filed on Nov. 5, 2013.

(51) Int. Cl.
*G01N 35/00* (2006.01)
*G01N 35/02* (2006.01)
(Continued)

(52) U.S. Cl.
CPC .... *G01N 35/00663* (2013.01); *B01L 3/50853* (2013.01); *B01L 3/523* (2013.01);
(Continued)

(58) Field of Classification Search
CPC ....... B01L 2200/023; B01L 2200/0689; B01L 2200/16; B01L 2300/041; B01L 2300/042;
(Continued)

(56) References Cited

U.S. PATENT DOCUMENTS

| 4,713,064 A | 12/1987 | Bruno et al. |
| 4,925,066 A | 5/1990 | Rosenbaum |

(Continued)

FOREIGN PATENT DOCUMENTS

| DE | 195 36 789 A1 | 4/1997 |
| EP | 0 252 632 A2 | 1/1988 |

(Continued)

OTHER PUBLICATIONS

PCT International Search Report and Written Opinion dated Feb. 19, 2015 (7 Pages).

(Continued)

*Primary Examiner* — Jennifer Wecker (57) ABSTRACT

A multi-well fluid container that includes a container body is provided for use in an in vitro diagnostics automation system. The container body includes a first well having a first well size configured to hold a first fluid and an openable first well closure that covers a first well opening. The first well opening provides access to the first fluid in the first well when the openable first well closure is opened. The container body also includes a second well having a second well size configured to hold a second fluid and having an openable second well closure that covers a second well opening. The second well opening provides access to the second fluid in the second well when the openable second well closure is opened. The first well size of the first well is different than the second well size of the second well.

14 Claims, 10 Drawing Sheets

(51) Int. Cl.
  *B01L 9/00* (2006.01)
  *B01L 3/00* (2006.01)
  *G01N 35/04* (2006.01)
  *G01N 35/10* (2006.01)

(52) U.S. Cl.
  CPC ............ *B01L 3/527* (2013.01); *G01N 35/025* (2013.01); *G01N 35/04* (2013.01); *B01L 3/5453* (2013.01); *B01L 2200/023* (2013.01); *B01L 2200/0689* (2013.01); *B01L 2200/142* (2013.01); *B01L 2200/16* (2013.01); *B01L 2300/021* (2013.01); *B01L 2300/041* (2013.01); *B01L 2300/042* (2013.01); *B01L 2300/08* (2013.01); *B01L 2300/0809* (2013.01); *G01N 2035/00673* (2013.01); *G01N 2035/0405* (2013.01); *G01N 2035/0413* (2013.01); *G01N 2035/0443* (2013.01); *G01N 2035/0455* (2013.01); *G01N 2035/1032* (2013.01)

(58) Field of Classification Search
  CPC ......... B01L 2300/08; B01L 2300/0809; B01L 3/50853; B01L 3/523; B01L 3/527; B01L 3/5453; B01L 2035/00673
  See application file for complete search history.

(56) References Cited

U.S. PATENT DOCUMENTS

| | | | | |
|---|---|---|---|---|
| 4,935,274 | A * | 6/1990 | DeBenedictis | B32B 27/08 206/538 |
| 4,970,053 | A * | 11/1990 | Fechtner | B01L 3/508 206/569 |
| 5,102,631 | A * | 4/1992 | Jordan | B01L 3/508 206/814 |
| 5,542,575 | A * | 8/1996 | Stark | B65D 47/286 220/348 |
| 5,578,494 | A * | 11/1996 | Clark | B01F 11/0022 215/235 |
| 5,632,399 | A * | 5/1997 | Palmieri | B01L 3/50853 220/253 |
| 5,885,530 | A * | 3/1999 | Babson | B01L 3/50853 422/63 |
| 6,060,022 | A | 5/2000 | Pang et al. | |
| 6,149,872 | A | 11/2000 | Mack et al. | |
| 6,645,423 | B2 | 11/2003 | Everette et al. | |
| 6,857,530 | B2 | 2/2005 | Yourist | |
| 7,235,163 | B2 | 6/2007 | Ramstad et al. | |
| 8,197,776 | B2 | 6/2012 | Nuotio et al. | |
| 3,361,387 | A1 | 1/2013 | Schacher et al. | |
| 8,728,413 | B2 * | 5/2014 | Talmer | B01F 11/0002 422/547 |
| 2003/0044323 | A1 | 3/2003 | Diamond et al. | |
| 2004/0071595 | A1 | 4/2004 | Neeper et al. | |
| 2005/0013737 | A1 | 1/2005 | Chow et al. | |
| 2006/0172433 | A1* | 8/2006 | Motadel | B01L 3/0241 436/180 |
| 2006/0235335 | A1* | 10/2006 | Elsenhans | B01L 3/502707 600/577 |
| 2008/0251489 | A1 | 10/2008 | Livingston et al. | |
| 2009/0003981 | A1 | 1/2009 | Miller | |
| 2009/0117004 | A1 | 5/2009 | Fritchie et al. | |
| 2010/0233035 | A1* | 9/2010 | Denawa | G01N 35/1002 422/509 |
| 2011/0009608 | A1 | 1/2011 | Kim et al. | |
| 2011/0268627 | A1 | 11/2011 | Warhurst et al. | |
| 2011/0271773 | A1 | 11/2011 | Komatsu et al. | |
| 2011/0293478 | A1 | 12/2011 | Robert et al. | |

FOREIGN PATENT DOCUMENTS

| | | | |
|---|---|---|---|
| EP | 0252632 | A2 * | 1/1988 |
| EP | 1 895 305 | A1 | 3/2008 |

OTHER PUBLICATIONS

Extended EP Search Report dated Oct. 9, 2017 of corresponding European Application No. 14860937.3, 4 pages.

\* cited by examiner

MULTI-WELL WEDGE-SHAPED REAGENT CONTAINER WITH AUTO-OPEN CAPABILITY

CROSS-REFERENCE TO RELATED APPLICATIONS

This application claims priority to U.S. provisional application Ser. No. 61/900,209 filed Nov. 5, 2013, which is incorporated herein by reference in its entirety.

TECHNOLOGY FIELD

Embodiments disclosed herein relate in general to systems and methods for aligning containers and, more particularly, to systems and methods for aligning wedge containers and anti-evaporation tubes within the wedge containers in a server ring for in vitro diagnostics in a clinical analyzer.

BACKGROUND

In vitro diagnostics (IVD) allows labs to assist in the diagnosis of disease based on assays performed on patient fluid samples. IVD includes various types of analytical tests and assays typically conducted with automated clinical chemistry analyzers (analyzers) onto which fluid containers, such as tubes or vials containing patient samples, have been loaded. The analyzer extracts a fluid sample from the vial and combines the sample with various reagent fluids (reagents) in special reaction cuvettes or tubes (referred to generally as reaction vessels).

In some conventional systems, reagent inventory on analyzers is provided using wedge-shaped reagent containers (containers) arrayed in storage areas, such as a circular server assembly (server). The containers are held in slots within the circular server. The wedge-shape allows for an efficient utilization of reagent storage volume so that the maximum number of containers can be stored on board the analyzer and the maximum test menu may be available to the user. Reagents are typically packaged in different wedge-shaped containers such as low volume, mid-volume, and high volume depending on reagent stability and method use rate. The reagent containers typically have threaded necks for closure and are opened by removing a threaded closure and loaded into the servers manually. New containers are opened and manually loaded as analyzer.

SUMMARY

Embodiments provide a multi-well fluid container having a container body for use in an in vitro diagnostics automation system that includes a container body. The container body includes a first well having a first well size configured to hold a first fluid and an openable first well closure that covers a first well opening. The first well opening is configured to provide access to the first fluid in the first well when the openable first well closure is opened. The container body also includes a second well adjacent the first well. The second well has a second well size configured to hold a second fluid and having an openable second well closure that covers a second well opening that is separate from the first well opening. The second well opening is configured to provide access to the second fluid in the second well when the openable second well closure is opened. The first well size of the first well is different than the second well size of the second well.

According to one embodiment, the openable first well closure includes a first sealing portion configured to be automatically opened while on board an analyzer and the openable second well closure includes a second sealing portion configured to be automatically opened while on board the analyzer.

According to another embodiment, the openable first well closure is configured to be manually removed by an operator and the openable second well closure is configured to be manually removed by the operator.

In one embodiment, the container body is wedge-shaped and is further configured to be held in one of a plurality of substantially same sized wedged shaped compartments of a circular storage area.

In another embodiment, the first well is further configured to hold a low volume of the first fluid and the first well opening is configured to provide access to the low volume of the first fluid when the openable first well closure is opened. The second well is further configured to hold a high volume of the second fluid that is a larger volume than the low volume of the first fluid and the second well opening is further configured to provide access to the high volume of the second fluid when the openable second well closure is opened.

In an aspect of an embodiment, the multi-well fluid container further includes a third well configured to hold a mid-volume of a third fluid that is a larger volume than the low volume of the first fluid and a smaller volume than the high volume of the second fluid.

According to one embodiment, the multi-well fluid container further includes a third well adjacent to at least one of the first well and the second well. The third well has a third well size configured to hold a third fluid and an openable third well closure that covers a third well opening that is separate from the first well opening and the second well opening. The third well opening is configured to provide access to the third fluid in the third well when the openable third well closure is opened.

In yet another embodiment, the first well and the second well each include an anti-evaporation tube.

Embodiments provide an in vitro diagnostics automation system that includes a plurality of multi-well fluid containers each having substantially the same length and width and each of the plurality of multi-well fluid containers comprising a plurality of wells configured to hold a corresponding fluid. Each well has an openable closure that covers a corresponding opening configured to provide access to the corresponding fluid when the openable closure is opened. The system also includes a storage area having a plurality of compartments. Each of the plurality of compartments is configured to hold one of the plurality of multi-well fluid containers and having substantially the same length and width as the length and width of the plurality of multi-well fluid containers.

According to one embodiment, each openable closure is configured to be automatically opened while on board an analyzer.

According to another embodiment, each of the plurality of multi-well fluid containers has at least two different sized wells.

In one embodiment, the storage area is a circular storage area and each of the plurality of compartments in the circular storage area is wedged shaped and each of the plurality of multi-well fluid containers is wedge-shaped.

In another embodiment, the at least two different sized wells in each compartment are configured to hold different volumes of one or more fluids.

Embodiments provide a method of operating an in vitro diagnostics automation system. The method includes holding a multi-well fluid container having a plurality of different sized wells in one of a plurality of compartments of a storage area. Each well of the plurality of different sized wells has an openable closure covering a corresponding opening. The method also includes accessing a low volume of a first fluid from a first well of the plurality of different sized wells and accessing a high volume of a second fluid from a second well of the plurality of different sized wells. The high volume of the second fluid is a larger volume than the low volume of the first fluid. The method further includes opening the multi-well fluid container from the one of a plurality of compartments of the storage area.

According to one embodiment, the further includes opening an openable first closure from a first well of the plurality of different sized wells to provide access to the first fluid from the first well and opening an openable second closure from a second well of the plurality of different sized wells to provide access to the second fluid from the second well.

According to another embodiment, opening the openable first closure further includes automatically opening the openable first closure while on board an analyzer and opening the openable second closure further includes automatically opening the openable second closure while on board the analyzer.

In one embodiment, opening the multi-well fluid container from the one of the plurality of compartments of the storage area occurs after at least a portion of the low volume of the first fluid is accessed from the first well and at least a portion of the high volume of the second fluid is accessed from the second well.

In another embodiment, the method further includes accessing a mid-volume of a third fluid from a third well of the plurality of different sized wells. The mid-volume of the third fluid is larger than the low volume of the first fluid and smaller than the high volume of the second fluid.

In an aspect of an embodiment, opening the fluid container from the one of the plurality of compartments of the storage area occurs after at least a portion of the low volume of the first fluid is accessed from the first well. At least a portion of the high volume of the second fluid is accessed from the second well and at least a portion of the mid-volume of the third fluid is accessed from the third well.

In yet another embodiment, the method further includes opening a first sealing portion of the openable first closure using a first cannula to provide access to the low volume of the first fluid of the first well and opening a second sealing portion of the openable second closure using a second cannula to provide access to the high volume of the second fluid of the second well.

BRIEF DESCRIPTION OF THE DRAWINGS

The foregoing and other aspects of the embodiments disclosed herein are best understood from the following detailed description when read in connection with the accompanying drawings. For the purpose of illustrating the invention, there are shown in the drawings embodiments that are presently preferred, it being understood, however, that the embodiments disclosed herein are not limited to the specific instrumentalities disclosed. Included in the drawings are the following Figures.

DESCRIPTION OF EXEMPLARY EMBODIMENTS

Testing may include a number of different reagent methods. During each of these methods, one or more reagents may be used. Further, different volumes of reagents may be needed for different reagent methods, causing some reagents to be used more than other reagents. Some conventional systems use same sized single-welled containers, each holding specific reagents, which are placed in equally sized compartments of a circular server. Some reagents may, however, have different expiration rates and different levels of open well stability. Therefore, in these conventional systems, some of the lesser used reagents having shorter expiration rates and/or lower levels of open well stability may become unusable reagents after the single-welled containers are opened.

Some conventional systems use different sized bottles to hold the different volumes of reagents. The larger bottles are sized substantially the same as the equally sized compartments of the circular server. The smaller sized containers, however, are smaller than the equally sized compartments of the circular server and may include buffers (e.g., portions of the container that do not hold reagents) to fill in the unused space of the equally sized compartments and limit movement of the containers in the equally sized compartments. Because these smaller sized bottles include portions that are not used to hold reagents, the storage capacity is not maximized.

To address these shortcomings described above as well as others, embodiments described herein provide a multi-well fluid container that can accommodate different volume methods (e.g., low-volume, mid-volume, and high-volume methods) that make efficient use of the server storage capacity. In some embodiments, the multi-well container may be opened while in the reagent server so that individual wells can be accessed without affecting the stability of the un-opened wells. After a first well of a container is consumed, a second well may be opened and accessed.

Embodiments improve storage inefficiency and load frequency with multi-well containers that may be automatically loaded and opened in reagent servers. Embodiments disclosed herein provide a multi-well container that improves reliability by reducing the reagent loading and overall unloading frequency. Some embodiments reduce the cost of low and mid-volume containers because, for example, each of the multi-well low and mid-volume containers may be the equivalent of two single-well low and mid-volume containers at the about the same cost per container. Another cost benefit may result from using only one barcode label which can be a significant portion of the overall manufacturing cost.

Embodiments may include any number of wells, each having the same or different sizes. In some embodiments, multi-well containers may include reagents used for three or more reagent methods. In some embodiments, multi-well containers may include two or more wells, such as three wells, four wells or more.

In some embodiments, multi-well fluid containers may be used in an automation system, such as, for example, an in vitro diagnostics automation system described in PCT Patent Application US13/24,331, which is herein incorporated by reference. Embodiments may, however, include multi-well containers used in other types of environments.

In some embodiments, the automation system may include a storage area (e.g., server ring 300 shown in FIG. 3) for holding the multi-well wedge shaped fluid containers. The containers may be configured to be placed into one of a plurality of equally sized wedge-shaped compartments of the storage area with each compartment being configured to receive and hold a multi-well wedge shaped fluid container. The multi-well containers may be configured to hold one or more reagent fluids in the IVD automation system. The multi-well containers may be configured to hold other types of fluids (e.g., samples).

Figure 1:
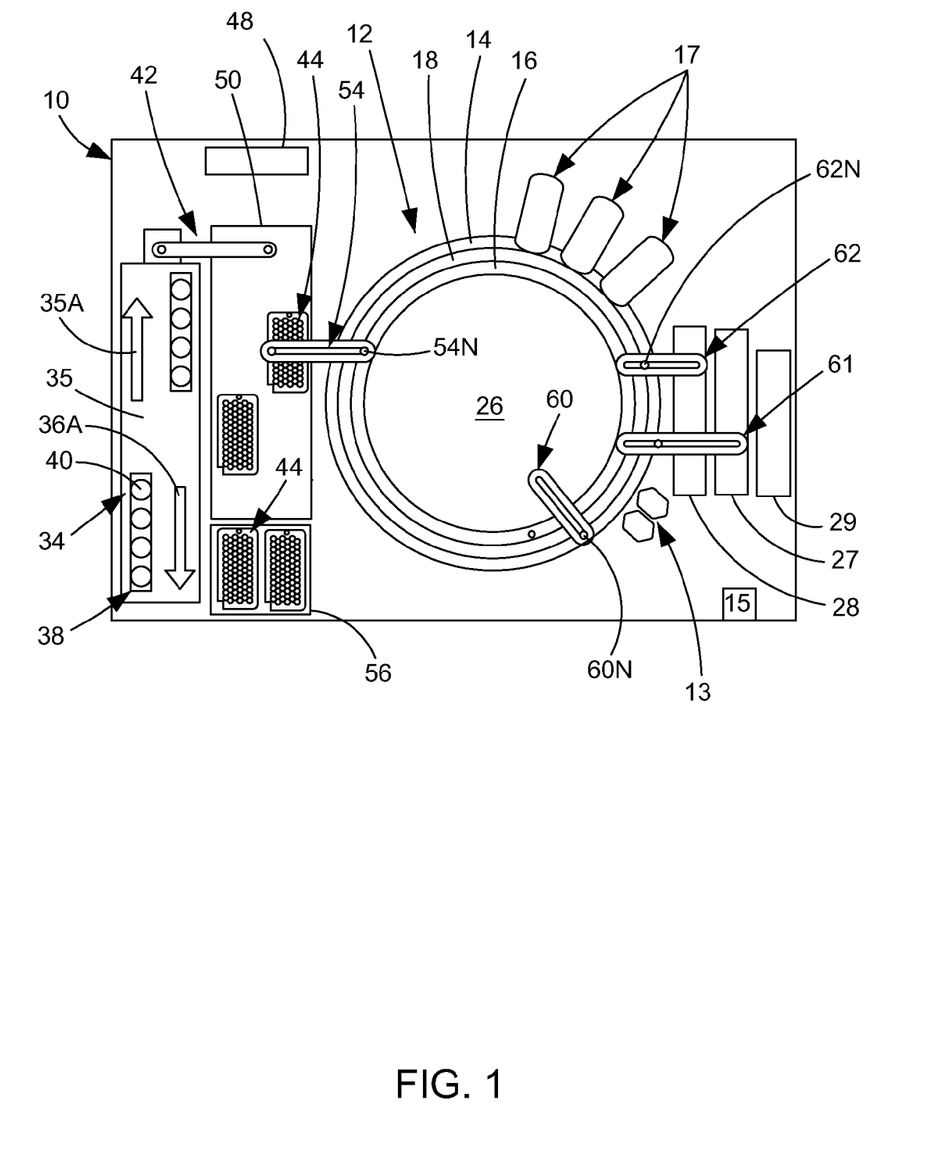
FIG. 1 is a top view of an exemplary chemistry analyzer in which embodiments of the multi-well containers may be employed.
Figure 2:
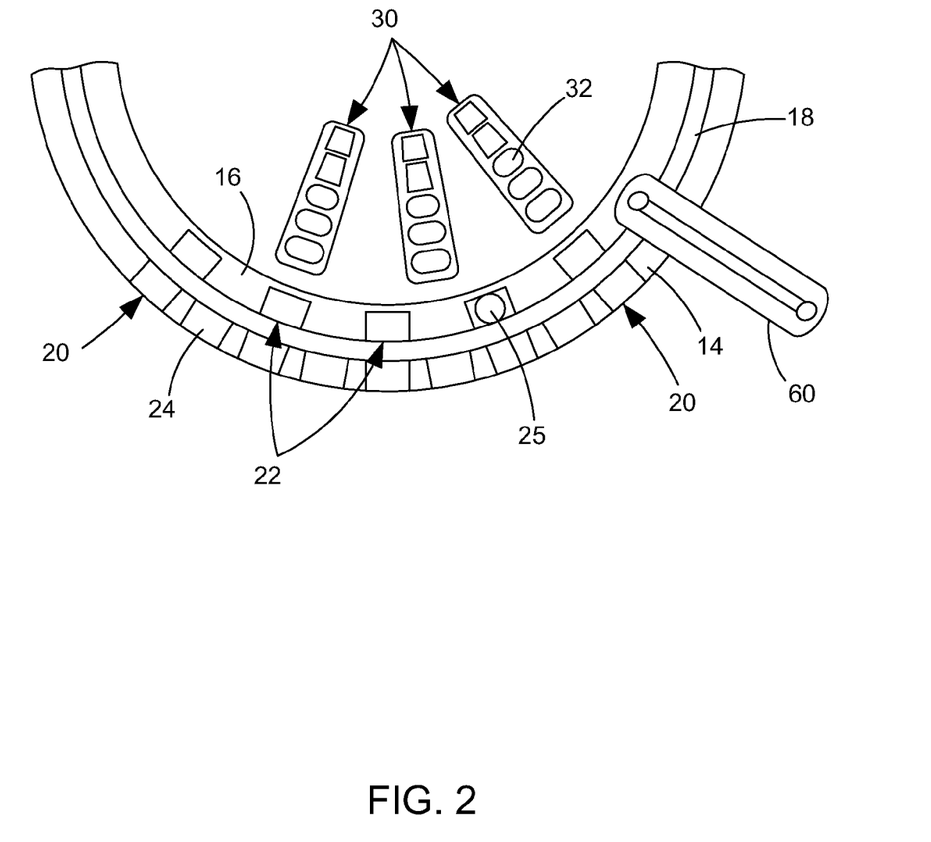
FIG. 2 is a top view of a portion of a carousel for transporting reaction vessels and cuvettes that can be used with the embodiments disclosed herein.

In one embodiment, multi-well wedge containers may be used in an automatic clinical chemistry analyzer (analyzer), such as analyzer 10 shown in FIG. 1. FIG. 1, taken with FIG. 2, shows schematically the elements of the analyzer 10, which may include, for example, the analyzer described in U.S. Pat. No. 7,258,480. Analyzer 10 comprises a reaction carousel 12 supporting an outer carousel 14 having cuvette ports 20 (represented in FIG. 2) formed therein and an inner carousel 16 having vessel ports 22 (represented in FIG. 2) formed therein, the outer carousel 14 and inner carousel 16 being separated by an open groove 18. Cuvette ports 20 are adapted to receive a plurality of reaction cuvettes 24, as represented in FIG. 2, that contain various reagents and sample liquids for conventional clinical chemistry and immunoassay assays. Vessel ports 22 can be adapted to receive a plurality of reaction vessels 25, as represented in FIG. 2, that contain specialized reagents for ultra-high sensitivity luminescent immunoassays. Cuvettes 24 and reaction vessels 25 can include bottom portions. While cuvettes and reaction vessels can have differing shapes, as used herein, the methods for mixing can be applied to the contents of reaction vessels 25 or cuvettes 24, and the terms reaction vessels and cuvettes should be considered broadly and interchangeably. Reaction vessels can include, for instance, cuvettes, vials, tubes, or other suitable vessels for mixing reagents and solutions.

Reaction carousel 12 is rotatable using stepwise movements in a constant direction, the stepwise movements being separated by a constant dwell time during which reaction carousel 12 remains stationary and computer controlled assay operational devices 13, such as sensors, reagent add stations, mixing stations, and the like, operate as needed on an assay mixture contained within a cuvette 24.

Analyzer 10 is controlled by software executed by a computer 15 based on computer programs written in a machine language like that used on the Dimension® clinical chemistry analyzer sold by Siemens Healthcare Diagnostics Inc. of Deerfield, Ill., and widely used by those skilled in the art of computer-based electromechanical control programming. Computer 15 also executes application software programs, such as the Dimension Vista® system software for performing assays conducted by various analyzing means 17 (e.g., detection units) within analyzer 10. Analyzing means 17 can include, for instance, one or more photometers, turbidimeters, nephelometers, electrodes, electromagnets, and/or LOCI® readers for interpreting the results of reactions within the reaction vessels 25 or cuvettes 24.

As seen in FIG. 1, a bi-directional incoming and outgoing sample fluid tube transport system 34 comprises a mechanism for transporting sample fluid tube racks 38 containing open sample fluid containers such as sample fluid tubes 40 from a rack input load position at a first end of the input lane 35 to the second end of input lane 35 as indicated by open arrow 35A. Liquid specimens contained in sample tubes 40 may be identified by reading bar coded indicia placed thereon using a conventional bar code reader to determine, among other items, a patient's identity, tests to be performed, if a sample aliquot is to be retained within analyzer 10, and, if so, for what period of time. It is also common practice to place bar coded or other indicia on sample tube racks 38 and employ a large number of bar code readers or other readers installed throughout analyzer 10 to ascertain, control, and track the location of sample tubes 40 and sample tube racks 38.

A conventional liquid sampling probe 42 is located proximate to the second end of the input lane 35 and is operable to aspirate aliquot portions of sample fluid from sample fluid tubes 40 and to dispense an aliquot portion of the sample fluid into one or more of a plurality of vessels in aliquot vessel array 44. This provides a quantity of sample fluid to facilitate assays and to provide for a sample fluid aliquot to be retained by analyzer 10 within an environmental chamber 48. After sample fluid is aspirated from all sample fluid tubes 40 on a rack 38 and dispensed into aliquot vessels in array 44 and maintained in an aliquot vessel array storage and transport system 50, rack 38 may be moved, as indicated by open arrow 36A, to a front area of analyzer 10 accessible to an operator so that racks 38 may be unloaded from analyzer 10.

Sample aspiration probe 54 is controlled by computer 15 and is adapted to aspirate a controlled amount of sample from individual aliquot vessels in array 44 positioned at a sampling location within a track (not shown) and is then shuttled to a dispensing location where an appropriate amount of aspirated sample is dispensed into one or more cuvettes 24 for testing by analyzer 10 for one or more analytes. After sample has been dispensed into reaction cuvettes 24, conventional transfer means move aliquot vessel arrays 44, as required, within aliquot vessel array storage and dispensing module 56 between aliquot vessel array storage and transport system 50, environmental chamber 48, and a disposal area (not shown).

Temperature-controlled storage areas or servers 26, 27, and 28 contain an inventory of multi-compartment elongated reagent cartridges 30 (shown in FIG. 2) loaded into the system via input tray 29, such as those described in U.S. Pat. No. 6,943,030 assigned to the assignee of the present invention. Cartridges 30 contain reagents in wells 32 to perform a number of different assays. Reagents may be moved and aligned within analyzer 10 by any conventional means, including those described in U.S. Patent Application Publication No. 2012/0127821, also assigned to the assignee of the present invention, and incorporated herein by reference. Computer 15 can control and track the motion and placement of the reagent cartridges 30. Reagents from server 26, 27, and 28 can be handled by one or more reagent probe arms 60, 61, and 62.

Figure 3:
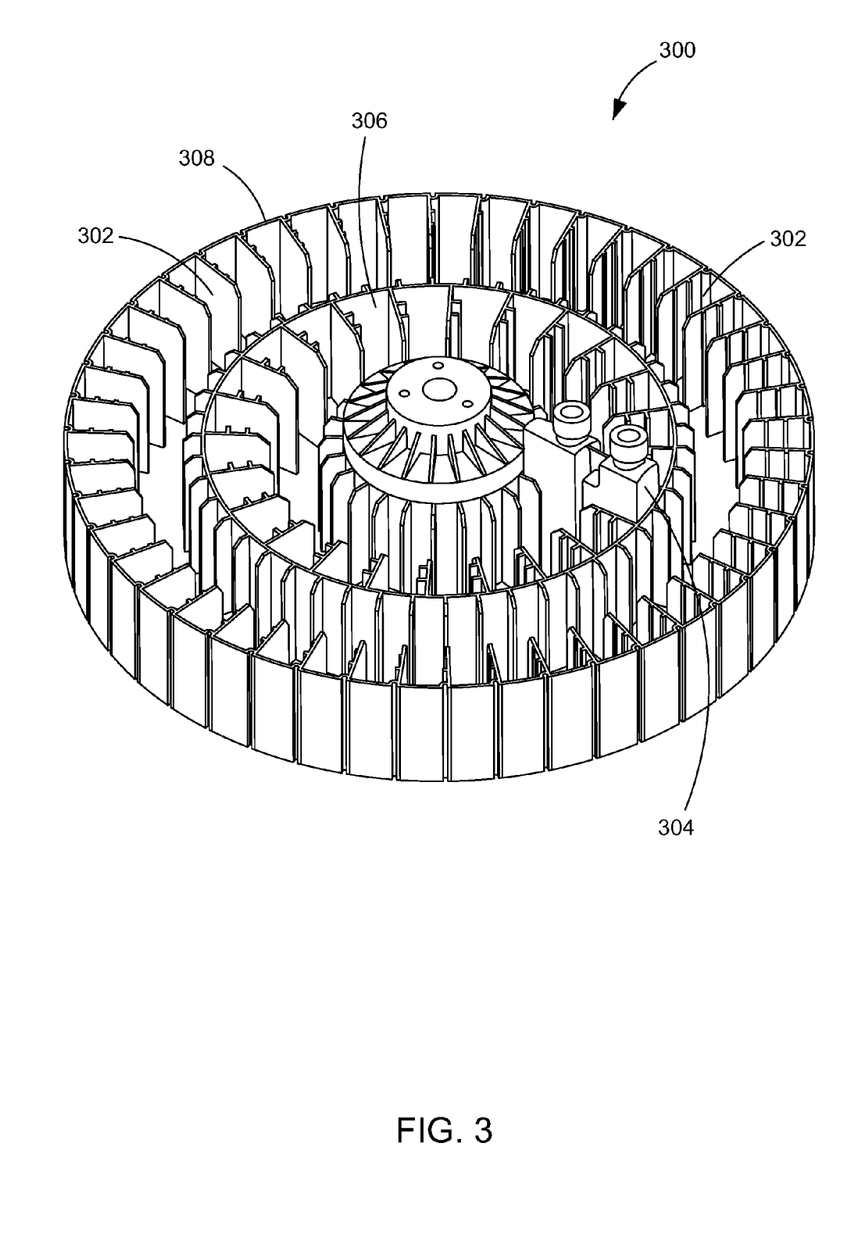
FIG. 3 is a perspective view of an exemplary server ring holding an exemplary multi-well container in a server ring compartment that can be used with embodiments disclosed herein.

FIG. 3 is a perspective view of an exemplary server ring 300 having a plurality of compartments 302 holding a multi-well fluid container 304. For simplicity, only one container 304 is shown in FIG. 3. In some embodiments, server ring 300 may hold any number of containers 304. In some embodiments, container 304 may be used to hold reagent fluids. In other embodiments, container 304 may be used to hold other fluids, such as patient samples. As shown in FIG. 3, the compartments 302 of a server ring 300 may be wedge-shaped and the container 304 may be wedge-shaped to fit securely within a corresponding compartment 302. Server ring 300 may be positioned at a center of a reaction carousel, such as at the center of the reaction carousel 12 shown in FIG. 1. In some embodiments, reagent server rings may be located on outer portions of carousels and the samples and/or cuvettes may be located on the inner portions of carousels. The server ring 300 shown in the embodiment in FIG. 3 includes an inner loop 306 and an outer loop 308. Embodiments may include any number of loops.

In some embodiments, a compartment 302 may be configured to limit movement of containers 304 during operation. For example, as shown in FIG. 3, a compartment 302 may be shaped substantially the same as each container 304. In some aspects, multi-well wedge containers 304 may each have the same outer surface geometries and configured to be placed into wedge-shaped compartments 302 of the server ring 300.

Figure 4A:
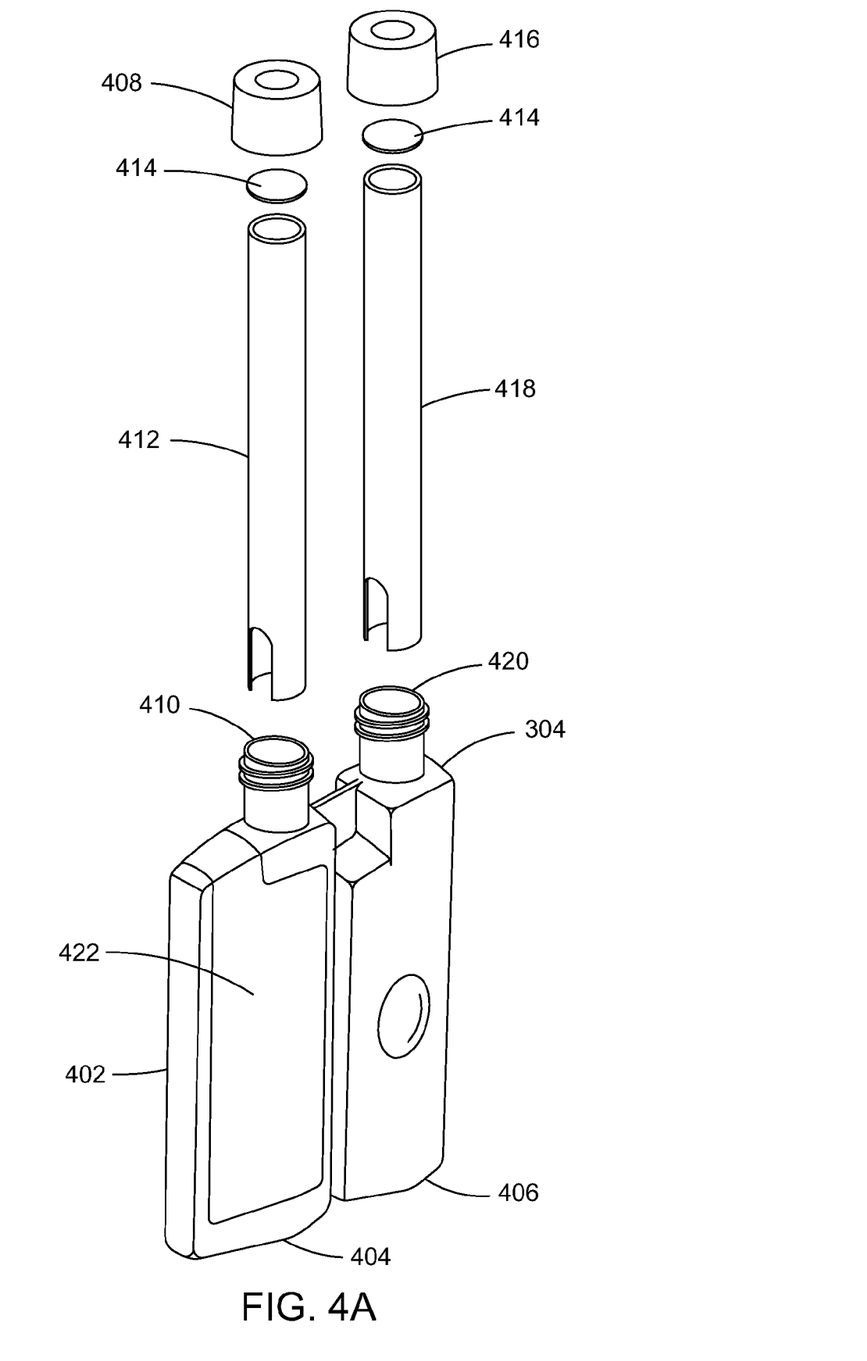
FIG. 4A is an exploded view of the exemplary multi-well container shown in FIG. 3.
Figure 4B:
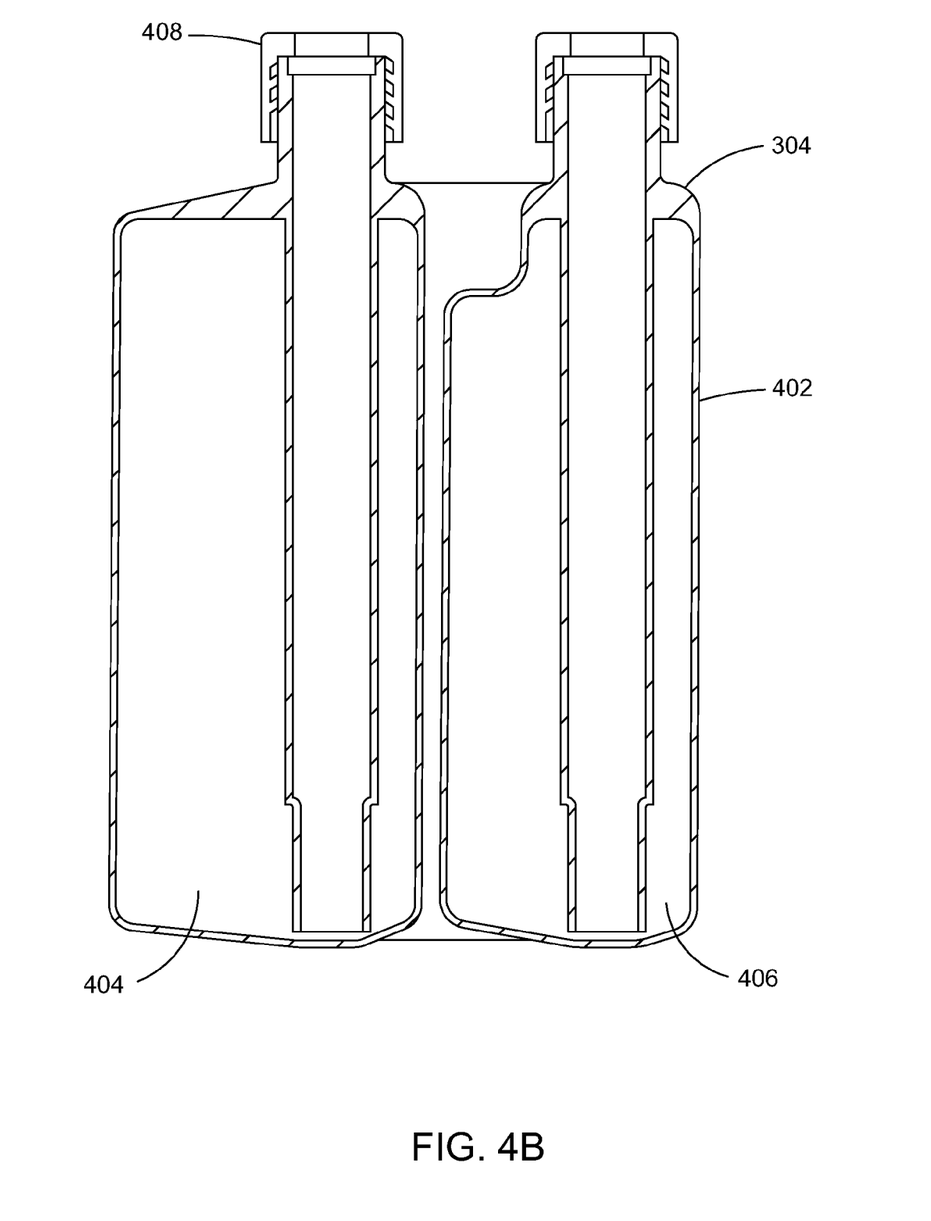
FIG. 4B is a right side view of the multi-well fluid container shown in FIG. 3.
Figure 4C:
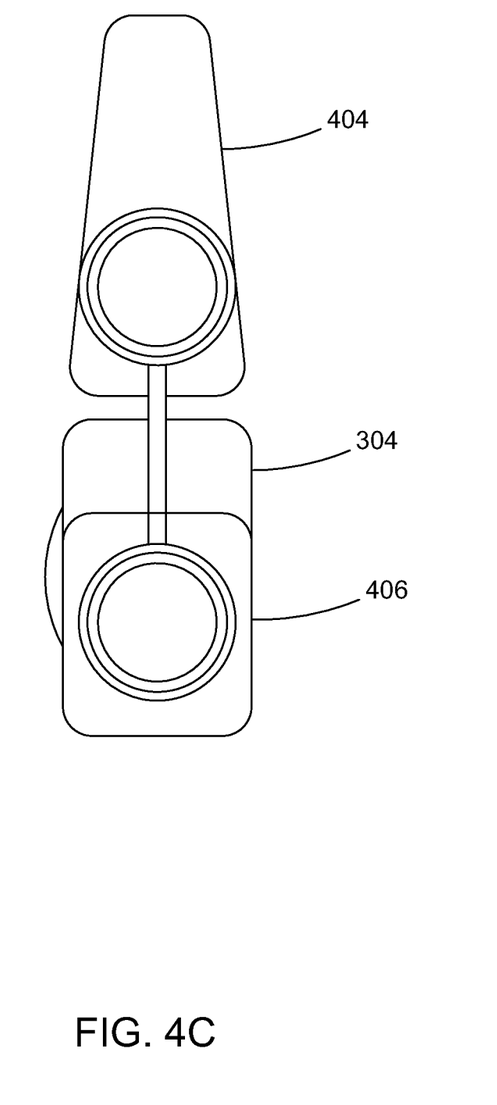
FIG. 4C is a top view of the multi-well fluid container shown in FIG. 3.
Figure 4D:
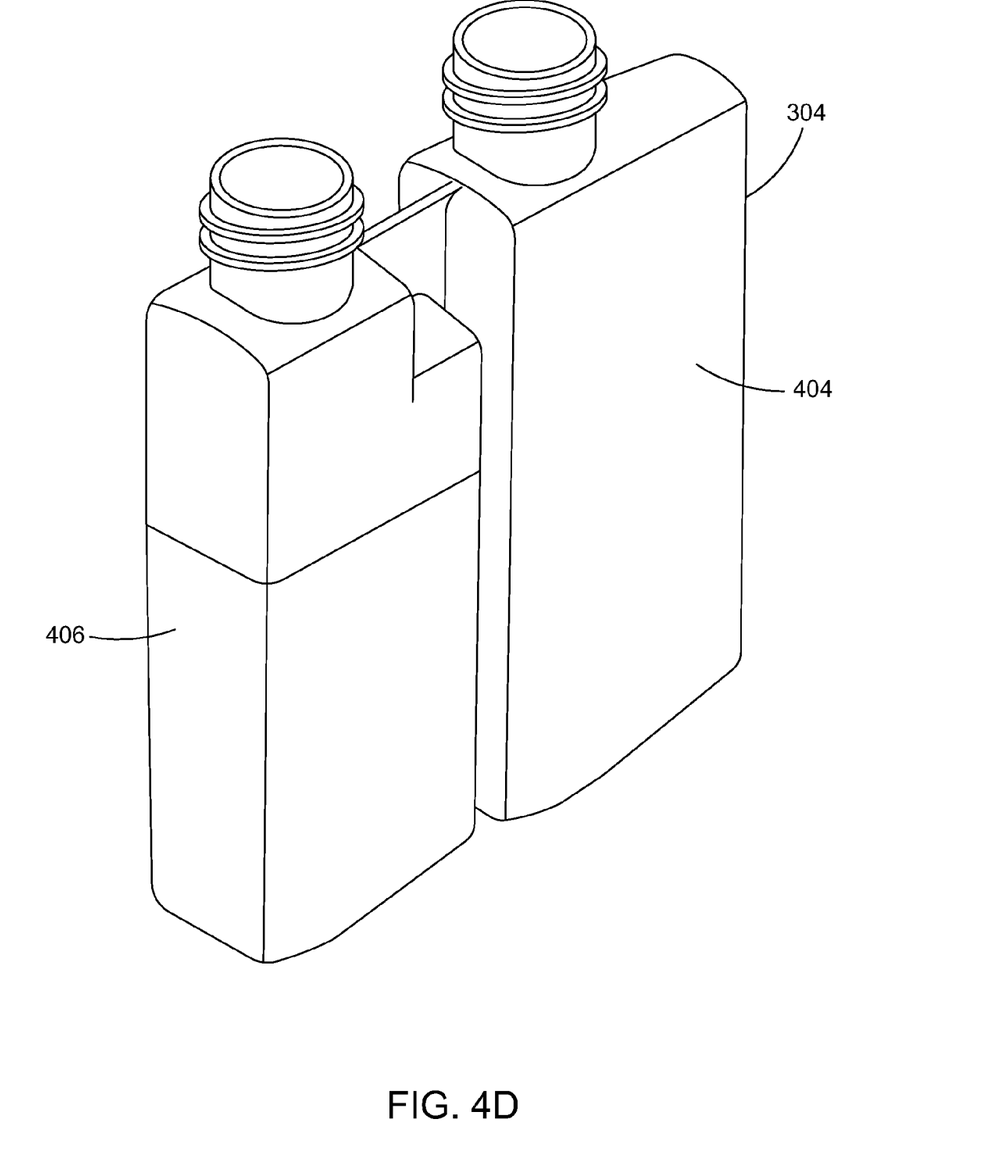
FIG. 4D is a perspective view of the multi-well fluid container shown in FIG. 3.
Figure 4E:
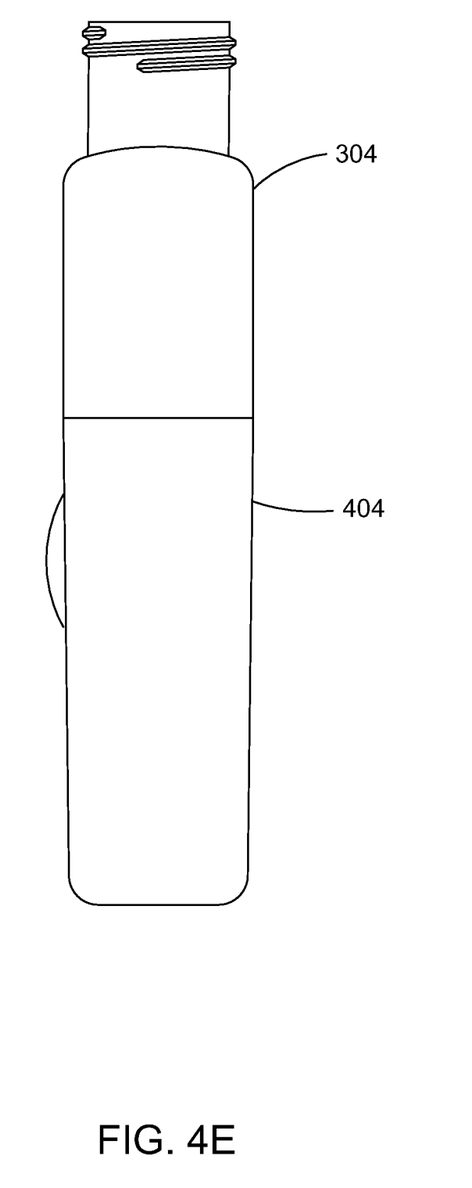
FIG. 4E is a rear view illustrating the rear of the second well of the multi-well fluid container shown in FIG. 3.
Figure 4F:
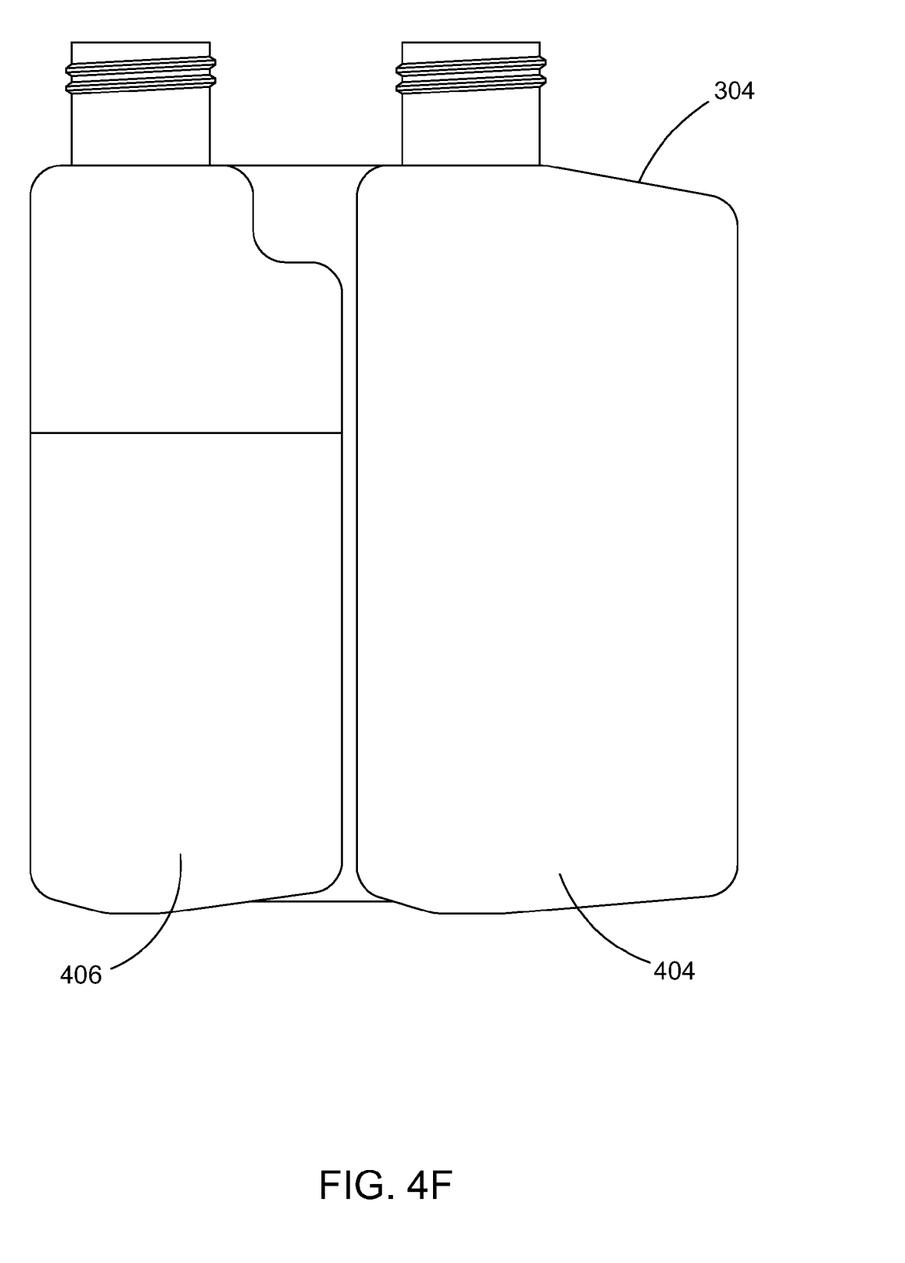
FIG. 4F is a left side view illustrating of the multi-well fluid container shown in FIG. 3.

FIG. 4A is an exploded view of the multi-well fluid container 304 shown in FIG. 3. FIG. 4B is a side view of the multi-well fluid container 304 shown in FIG. 3. FIG. 4C is a top view of the multi-well fluid container shown in FIG. 3. FIG. 4D is a perspective view of the multi-well fluid container shown in FIG. 3. FIG. 4E is a rear view illustrating the rear of the second well of the multi-well fluid container shown in FIG. 3. FIG. 4F is a left side view illustrating of the multi-well fluid container shown in FIG. 3.

As used herein, openable closures may be: (i) removable closures (e.g., threaded closures 408 removed by rotating and snap fit closures, magnetic closures and friction fit closures removed by pulling) that may be manually removed by an operator; and (ii) automatically openable closures (e.g., automatically openable closures in FIG. 5 that may include sealing portions 506 and 508 that may be opened by cannulas 510 and 512). As shown in FIG. 4A through FIG. 4E, container 304 may include a container body 402 that includes a first well 404 and a second well 406. First well 404 has a first well size configured to hold a first fluid (not shown). As shown in FIG. 4A, first well 404 has a removable first well closure 408 that covers a first well opening 410 when in a closed position. The first well opening 410 provides access to the first fluid in the first well when the removable first well closure 408 is removed from the closed position. In the embodiment shown in FIG. 4A, first well 404 may also hold a first anti-evaporation tube 412.

As shown in FIG. 4A and FIG. 4B, second well 406 is adjacent to first well 404 and has a second well size configured to hold a second fluid (not shown). In some embodiments, the second fluid may be the same as the first fluid. In other embodiments, the second fluid may be different from the first fluid. Second well 406 has a removable closure second well 416 that covers a second well opening 420 that is separate from the first well opening 410. The second well opening 420 is configured to provide access to the second fluid in the second well when the removable second well closure 416 is removed. Second well 404 may also be configured to hold a second anti-evaporation tube 418.

In some embodiments, the removable first well closure 408 and the removable second well closure 416 may include an induction seal film 414. Embodiments may include removable closures that are threaded, snap fit, or friction fit. As described below with regard to FIG. 5, embodiments may also include openable closures having openable sealing portions 504 and cannulas 502 configured to open the openable sealing portions.

In the embodiment shown in FIG. 4B, the first well size of the first well 404 is larger than the second well size of the second well 406. Embodiments may, however, include wells having the same size and shape.

For simplicity purposes, the container 304 shown in the embodiment at FIG. 4A and FIG. 4B includes two wells. Embodiments may, however, include containers having any number of wells (e.g., three wells, four wells, etc.). In some embodiments, each of the different sized wells 404 and 406 are configured to hold different volumes of reagents. For example, the first well 404 may be configured (e.g., sized) to hold a low volume of the first fluid. The second well 406 is further configured (e.g., sized) to hold a high volume of the second fluid that is a larger volume than the low volume of the first fluid. In embodiments, where more than two wells are used, a third sized well (not shown) may be configured to hold a mid-volume of a third fluid that is larger than the low volume of the first fluid and smaller than the high volume of the second fluid.

The size and shape of the wells of the multi-well container 304 shown in FIGS. 4A and 4B is merely exemplary. Embodiments may include multi-well containers with wells of any size and shape. In some embodiments, different wells may be used to hold different fluids. In other embodiments, different wells may be used to hold the same fluids.

As shown in FIG. 4A, multi-well container 304 may include a label 422 disposed on a well 404. The label 422 may include different types of information associated with the fluid in the well 404, such as the type of fluid, the amount of fluid, scheduling and other information. The label may include a bar code area, a radio frequency identification RFID area (e.g., tag, sticker and the like) or another type of electronic information disposed on the label 422. The label 422 shown in FIG. 4A is disposed on first well. 404. Embodiments may, however, include labels on any well and any number of wells of a multi-well container.

Figure 5:
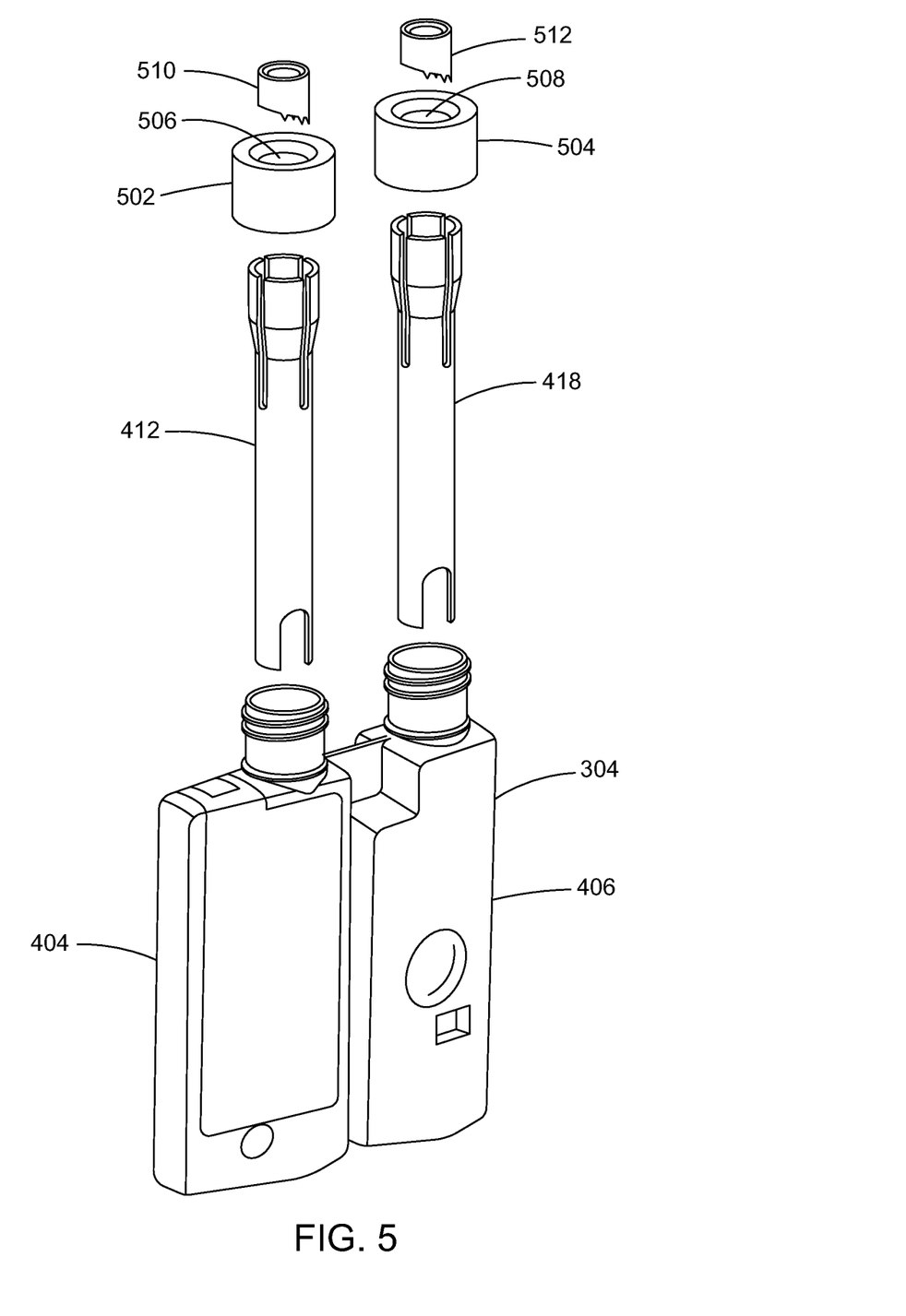
FIG. 5 is an exploded view of an exemplary multi-well fluid container having cap closures that include openable sealing portions and cannulas that can be used with embodiments disclosed herein.

FIG. 5 is an exploded view of an exemplary multi-well fluid container having cap closures 502 and 504 that include openable sealing portions 506 and 508 and cannulas 510 and 512 configured to open sealing portions 506 and 508 that can be used with embodiments disclosed herein. As shown in FIG. 5, removable closures 502 and 504 include corresponding sealing portions 506 and 508. Removable closures 502 and 504 may also include corresponding cannulas 510 and 512 configured to open sealing portions 506 and 508.

An in vitro diagnostics automation system may include one or more analyzers. As described above, multi-well wedge containers 304 may be used in an analyzer, such as analyzer 10 shown in FIG. 1. An exemplary method of operating an in vitro diagnostics automation system having an analyzer, such as analyzer 10, will now be described.

The exemplary method may include holding a multi-well fluid container 304 having first well 404 and second well 406 in one of a plurality of compartments 302 of a storage area, such as server ring 300. A first volume (e.g., low volume) of a first fluid may be accessed from the first well 404. In some embodiments, the first removable closure 408 shown in FIG. 4A may be removed from first well 404 to provide access to the first volume of the first fluid. In other embodiments, sealing portion 506 shown in FIG. 5 may be opened from the openable first closure 502 using cannula 510 to provide access to the first volume of the first fluid.

The removable second closure 416 may then be removed from second well 406 and a second volume (e.g., high volume being a larger volume than the low volume of the first fluid) of a second fluid may be accessed from the second well of the plurality of different sized wells. In some embodiments, the removable second closure 416 shown in FIG. 4A may be removed from second well 406 to provide access to the second volume of the second fluid. In other embodiments, sealing portion 508 shown in FIG. 5 may be opened from the openable second closure 504 using cannula 512 to provide access to the second volume of the second fluid. The multi-well fluid container 304 may then be removed from the compartment 302 of the server ring 300.

Embodiments may include accessing fluids from wells in any order. For example, openable second closures (e.g., removable closure 416 and openable closure 504) may be opened and the second volume of the second fluid may be accessed prior to removing openable first closures (e.g., removable closure 408 and openable closure 502) and accessing the first volume of the first fluid.

In some embodiments, the removable first closure 408 and the removable second closure 416 may be automatically removed (e.g., by a pick and place device not shown) while on board the analyzer 10. In other embodiments, however, the removable first closure 408 and the removable second closure 416 may be manually removed.

In some embodiments, the method may also include accessing a mid-volume of a third fluid from a third well of containers. As described above, the mid-volume of the third fluid may be larger than the low volume of the first fluid and smaller than the high volume of the second fluid.

In some embodiments, removing the fluid container 304 from the compartment 302 occurs after at least some portions of fluids are removed from each well 404 and 406 of a container 304. In other embodiment, container 304 may be removed from the compartment 302 may occur before portions of fluids are removed from each well 404 and 406 of a container 304.

As described above, some reagents may have different expiration rates. Reagents used less frequently but having shorter expiration rates may be held within smaller wells of the container 304. Because the volumes of these reagents are lower, lower volumes of the reagents are likely to expire, thus decreasing the amount of unusable remaining reagents.

As further described above, some reagents may have different levels of open well stability. The less frequently used reagents having low-level open well stability may also be held within the smaller un-opened wells (e.g., well 406), of the container 304. Because smaller volumes of the low-level open well stability reagents are stored in the smaller wells (e.g., well 406), these reagents are likely to be exposed for shorter amounts of time after the wells are opened. Accordingly, the likelihood of these reagents evaporating or becoming unstable due to exposure after the smaller wells (e.g., well 406) are opened decreases, and in turn, decreases the amount of unusable remaining reagents.

Because equally sized containers 304 are stored in server ring 300 having equally sized compartments 302, a more efficient storage capacity may be obtained than with reagent bottles of different sizes (e.g., no wasted space). Further, when a reagent in a well (e.g., 404) is empty, a probe (not shown) may move to the next opening to access another well (e.g., 406) of the multi-welled wedge container 304 rather than having to remove and replace the container 304 in the server ring 300, making scheduling easier and more efficient.

Embodiments are not limited to those disclosed. Those skilled in the art will appreciate that numerous changes and modifications may be made to the preferred embodiments disclosed herein and that such changes and modifications may be made without departing from the true spirit of the embodiments disclosed herein. It is therefore intended that the appended claims be construed to cover all such equivalent variations as fall within the true spirit and scope of the embodiments disclosed herein.

What is claimed is:

1. A multi-well fluid container for use in an in vitro diagnostics automation system comprising:
 a container body comprising:
  a first well having a first well size configured to hold a first fluid and having an openable first well closure that covers a first well opening, wherein the openable first well closure comprises:
   a first threaded cap configured to be manually removable by an operator; and
   a first openable sealing portion and a first cannula configured to be automatically opened and provide access to the first fluid in the first well via the first well opening when the openable first well closure is fitted on the first well opening and when the container is on board an analyzer; and
  a second well adjacent to the first well, the second well having a second well size configured to hold a second fluid and having an openable second well closure that covers a second well opening that is separate from the first well opening, wherein the openable second well closure comprises:
   a second threaded cap configured to be manually removable by an operator; and
   a second openable sealing portion and a second cannula configured to be automatically opened and provide access to the second fluid in the second well via the second well opening when the openable second well closure is fitted on the second well opening and when the container is on board the analyzer;
 wherein the first well size of the first well is different than the second well size of the second well.

2. The multi-well fluid container of claim 1, wherein the container body is wedge-shaped and is further configured to be held in one of a plurality of substantially same sized wedged shaped compartments of a circular storage area.

3. The multi-well fluid container of claim 1, wherein the first well is further configured to hold a low volume of the first fluid; and
 the second well is further configured to hold a high volume of the second fluid that is a larger volume than the low volume of the first fluid.

4. The multi-well fluid container of claim 3, further comprising a third well configured to hold a mid-volume of a third fluid that is a larger volume than the low volume of the first fluid and a smaller volume than the high volume of the second fluid.

5. The multi-well fluid container of claim 1, further comprising a third well adjacent to at least one of the first well and the second well, the third well having a third well size configured to hold a third fluid and having an openable third well closure that covers a third well opening that is separate from the first well opening and the second well opening, wherein the openable third well closure comprises:
- a third threaded cap configured to be manually removable by an operator; and
- a third openable sealing portion and a third cannula configured to be automatically opened and provide access to the third fluid in the third well via the third well opening when the openable third well closure is fitted on the third well opening and when the container is on board the analyzer.

6. The multi-well fluid container of claim 1, wherein the first well and the second well each comprise an anti-evaporation tube.

7. An in vitro diagnostics automation system comprising:
- a plurality of multi-well fluid containers each having substantially the same length and width and each of the plurality of multi-well fluid containers comprising a plurality of wells configured to hold a corresponding fluid, each well having an openable closure that covers a corresponding opening, the openable closure comprising a threaded cap configured to be manually removable by an operator, and an openable sealing portion and a cannula configured to be automatically opened and provide access to the corresponding fluid via the corresponding opening when the openable closure is fitted on the corresponding opening and when a corresponding one of the plurality of multi-well fluid containers is on board an analyzer; and
- a storage area having a plurality of compartments, each of the plurality of compartments configured to hold one of the plurality of multi-well fluid containers and having substantially the same length and width as the length and width of the plurality of multi-well fluid containers.

8. The automation system of claim 7, wherein each of the plurality of multi-well fluid containers has at least two different sized wells.

9. The automation system of claim 7, wherein the storage area is a circular storage area, each of the plurality of compartments in the circular storage area is wedged shaped, and each of the plurality of multi-well fluid containers is wedge-shaped.

10. The automation system of claim 7, wherein the at least two different sized wells in each compartment are configured to hold different volumes of one or more fluids.

11. A method of operating an in vitro diagnostics automation system, the method comprising:
- holding a multi-well fluid container having a plurality of different sized wells in one of a plurality of compartments of a storage area, each well of the plurality of different sized wells having an openable closure covering a corresponding opening, the openable closure comprising a threaded cap configured to be manually removable by an operator, and an openable sealing portion and a cannula that is configured to be automatically opened;
- accessing a low volume of a first fluid from a first well of the plurality of different sized wells via the corresponding opening when the corresponding openable closure is fitted on the corresponding opening, the corresponding openable sealing portion is opened, and the multi-well fluid container is on board an analyzer;
- accessing a high volume of a second fluid from a second well of the plurality of different sized wells, the high volume of the second fluid being a larger volume than the low volume of the first fluid, via the corresponding opening when the corresponding openable closure is fitted on the corresponding opening, the corresponding openable sealing portion is opened, and the multi-well fluid container is on board an analyzer; and
- opening the multi-well fluid container from the one of a plurality of compartments of the storage area.

12. The method of claim 11, wherein opening the multi-well fluid container from the one of the plurality of compartments of the storage area occurs after at least a portion of the low volume of the first fluid is accessed from the first well and at least a portion of the high volume of the second fluid is accessed from the second well.

13. The method of claim 11, further comprising accessing a mid-volume of a third fluid from a third well of the plurality of different sized wells, the mid-volume of the third fluid being larger than the low volume of the first fluid and smaller than the high volume of the second fluid.

14. The method of claim 13, wherein opening the fluid container from the one of the plurality of compartments of the storage area occurs after at least a portion of the low volume of the first fluid is accessed from the first well, at least a portion of the high volume of the second fluid is accessed from the second well, and at least a portion of the mid-volume of the third fluid is accessed from the third well.

* * * * *